US012390410B2

(12) United States Patent
Chopra (10) Patent No.: US 12,390,410 B2
(45) Date of Patent: Aug. 19, 2025

(54) COMPOUNDS, COMPOSITIONS AND METHODS FOR THE TREATMENT OR PREVENTION OF HAIR LOSS

(71) Applicant: Sunil Chopra, London (GB)

(72) Inventor: Sunil Chopra, London (GB)

(73) Assignee: LONDON DERMATOLOGY CENTRE INNOVATION LTD, London (GB)

( * ) Notice: Subject to any disclaimer, the term of this patent is extended or adjusted under 35 U.S.C. 154(b) by 344 days.

(21) Appl. No.: 17/924,389

(22) PCT Filed: May 27, 2021

(86) PCT No.: PCT/GB2021/051295
§ 371 (c)(1),
(2) Date: Nov. 10, 2022

(87) PCT Pub. No.: WO2021/240163
PCT Pub. Date: Dec. 2, 2021

(65) Prior Publication Data
US 2023/0172833 A1    Jun. 8, 2023

(30) Foreign Application Priority Data
May 28, 2020 (GB) ..................... 2008040

(51) Int. Cl.
| | | |
|---|---|---|
| A61K 8/64 | (2006.01) | |
| A61K 8/04 | (2006.01) | |
| A61K 8/55 | (2006.01) | |
| A61K 8/92 | (2006.01) | |
| A61Q 5/00 | (2006.01) | |
| A61Q 5/06 | (2006.01) | |
| A61Q 7/00 | (2006.01) | |

(52) U.S. Cl.
CPC ............... *A61K 8/64* (2013.01); *A61K 8/042* (2013.01); *A61K 8/046* (2013.01); *A61K 8/553* (2013.01); *A61K 8/92* (2013.01); *A61Q 5/002* (2013.01); *A61Q 5/065* (2013.01); *A61Q 7/00* (2013.01)

(58) Field of Classification Search
CPC .......... A61K 8/64; A61K 8/042; A61K 8/046; A61K 8/553; A61K 8/92; A61K 8/14; A61K 8/602; A61K 8/63; A61K 38/14; A61Q 5/002; A61Q 5/065; A61Q 7/00; A61P 17/14
See application file for complete search history.

(56) References Cited

U.S. PATENT DOCUMENTS

2018/0050080 A1    2/2018    Rotunda

FOREIGN PATENT DOCUMENTS

| CN | 106729614 A | | 5/2017 | |
|---|---|---|---|---|
| GB | 2398495 A | * | 8/2004 | ............ A61K 38/14 |
| WO | 02/059080 A2 | | 8/2002 | |
| WO | 02/094745 A2 | | 11/2002 | |

OTHER PUBLICATIONS

Van Dyk et. al. "A clinical evaluation of the agent on its own or in combination with mitomycin C" SA Medical Journal, Dec. 9, 1972, 1921-1926. (Year: 1972).*
Saitta et. al. "Bleomycin in Dermatology: A Review of Intralesional Applications." Dermatol Surg 2008; 34; 1299-1313. (Year: 2008).*
Adil et. al. "The effectiveness of treatments for androgenetic alopecia: A systematic review and meta-analysis." J Am Acad Dermatol, vol. 77, No. 1, Jul. 2017, 136-141. (Year: 2017).*
Yamamoto. "Bleomycin and the skin" British Journal of Dermatology 2006 155, pp. 869-875. (Year: 2006).*
Van Dyk et al. "Bleomycin" SA Medical Journal. Dec. 9, 1972. 1921+. (Year: 1972).*
Saitta et al. "Bleomycin in Dermatology", 2008, 1299+. (Year: 2008).*
Amin et al., "Alopecia areata: A review." Journal of the Saudi Society of Dermatology & Dermatologic Surgery 17.2 (2013): 37-45.
Bublin et al., "Drug-induced hair colour changes." Journal of clinical pharmacy and therapeutics 17.5 (1992): 297-302.
Saitta et al. "Bleomycin in dermatology: a review of intralesional applications." Dermatologic Surgery 34.10 (2008): 1299-1313.
York et al. "A review of the treatment of male pattern hair loss." Expert opinion on pharmacotherapy 21.5 (2020): 603-612.

* cited by examiner

*Primary Examiner* — Ali Soroush
*Assistant Examiner* — Rajan Pragani
(74) *Attorney, Agent, or Firm* — NIXON PEABODY LLP; David S. Resnick; Nicole D. Kling (57) ABSTRACT

The present disclosure relates to bleomycin for use in the treatment and/or prevention of hair loss and to a composition comprising bleomycin for use in the treatment and/or prevention of hair loss. A non-therapeutic method for promoting hair generation and/or hair growth is also disclosed, the method comprising administering or applying bleomycin or a composition comprising bleomycin to an area on the subject where the promotion of hair generation and/or hair growth is desired. Further disclosed is a non-therapeutic method for darkening hair, the method comprising administering or applying bleomycin or a composition comprising bleomycin to an area on the subject where darkening of hair is desired.

10 Claims, 8 Drawing Sheets

| | Intra-follicular distance(mm) | T:V Ratio | Follicle count per cm² | Average hairs per follicular unit | Average hair width (μm) |
|---|---|---|---|---|---|
| Temporal | 1.37 | 2.7 : 1 | 70 | 0.7 | 53.6 |
| Vertex | 1.61 | 1.0 : 1 | 47 | 0.6 | 39.9 |
| Occipital | 1.67 | NA | 34 | 1.0 | 65.9 |

Temporal    Vertex    Occipital

Hair count per cm²    Sum of hair widths(μm) per cm²

T:38  T:14  T:34  T:2392  T:798  T:2257
T+V:52  T+V:28  T+V:34  T+V:2738  T+V:1104  T+V:2257

▨ > 90 μm
large terminal

▤ 60-90 μm
intermediate terminal

▥ 30-60 μm
small terminal

▨ < 30 μm
vellus/miniaturized

Temporal  Vertex  Occipital    Temporal  Vertex  Occipital

Figure 5

|  | Intra-follicular distance(mm) | T:V Ratio | Follicle count per cm² | Average hairs per follicular unit | Average hair width (μm) |
|---|---|---|---|---|---|
| Temporal | 1.86 | NA | 34 | 1.3 | 76.3 |
| Vertex | 1.70 | NA | 48 | 1.4 | 80.2 |
| Occipital | 1.55 | 49.5:1 | 55 | 1.7 | 85.8 |

Temporal　　　　　Vertex　　　　　Occipital

Hair count per cm²　　　　Sum of hair widths(μm) per cm²
T: 43　T: 68　T: 89　　　T: 3311　T: 5474　T: 7788
T+V: 43　T+V:68　T+V: 91　T+V: 3311　T+V: 5474　T+V: 7836

▨ > 90 μm
large terminal

▤ 60-90 μm
intermediate terminal

▥ 30-60 μm
small terminal

▧ < 30 μm
vellus/miniaturized

Temporal　Vertex　Occipital　　Temporal　Vertex　Occipital

Figure 6

| | Intra-follicular distance(mm) | T:V Ratio | Follicle count per cm$^2$ | Average hairs per follicular unit | Average hair width (μm) |
|---|---|---|---|---|---|
| Temporal | 1.28 | 3.0 : 1 | 81 | 1.5 | 46.5 |
| Vertex | 1.25 | 6.0 : 1 | 94 | 1.5 | 55.3 |
| Occipital | 1.75 | 2.8 : 1 | 36 | 1.8 | 53.6 |

Temporal　　　　　Vertex　　　　　Occipital

Hair count per cm$^2$　　　　　Sum of hair widths(μm) per cm$^2$
T: 89　　T: 118　　T: 48　　T: 4837　　T: 7108　　T: 3042
T+V: 119　T+V: 138　T+V: 65　T+V: 5598　T+V: 7607　T+V: 3495

Figure 7

|  | Intra-follicular distance(mm) | T:V Ratio | Follicle count per cm$^2$ | Average hairs per follicular unit | Average hair width (μm) |
|---|---|---|---|---|---|
| Temporal | 1.74 | NA | 47 | 1.2 | 76.3 |
| Vertex | 1.50 | 14.8 : 1 | 55 | 1.6 | 60.8 |
| Occipital | 1.72 | NA | 52 | 1.7 | 82.8 |

Temporal     Vertex     Occipital

Hair count per cm$^2$      Sum of hair widths(μm) per cm$^2$ T: 55    T: 82    T: 89     T: 4187    T: 5199    T: 7393

T+V: 55   T+V: 88   T+V: 89   T+V: 4187   T+V: 5358   T+V: 7393

▨ > 90 μm
large terminal

▬ 60-90 μm
intermediate terminal

▦ 30-60 μm
small terminal

▨ < 30 μm
vellus/miniaturized

Figure 8

COMPOUNDS, COMPOSITIONS AND METHODS FOR THE TREATMENT OR PREVENTION OF HAIR LOSS

CROSS-REFERENCE TO RELATED APPLICATIONS

This application is a 35 U.S.C. § 371 National Phase Entry Application of International Application No. PCT/GB2021/051295 filed May 27, 2021, which designates the U.S. and claims benefit under 35 U.S.C. § 119 (a) of G.B. Provisional Application No. 2008040.4 filed May 28, 2020, the contents of which are incorporated herein by reference in their entireties.

FIELD OF THE INVENTION

The present disclosure relates to compounds, compositions and methods for the treatment and/or prevention of hair loss, for promoting hair generation and/or hair growth, and for darkening hair colour.

BACKGROUND OF THE INVENTION

It is natural to lose hair, typically between 50 and 100 hairs a day are lost, often without noticing, and it is a normal part of the ageing process. However, sometimes hair loss can be due to a reason other than ageing, such as a medical condition. The severity of hair loss can vary from a small area to the entire body.

Common types of hair loss include male-pattern baldness, female-pattern baldness, alopecia areata, and a thinning of the hair known as telogen effluvium. The cause of male-pattern baldness is a combination of genetics and male hormones, the cause of female-pattern baldness is unclear, the cause of alopecia areata is autoimmune, and the cause of telogen effluvium is typically a physically or psychologically stressful event. Telogen effluvium is very common following pregnancy.

Less common causes of hair loss include weight loss, certain medications including chemotherapy, iron deficiency, skin conditions, fungal infection, lupus erythematosus, hypothyroidism, hyperthyroidism, diabetes, radiation therapy, trauma and sarcoidosis, amongst others.

Hair loss can in some people cause psychological distress, resulting in changes in self-concept and body image.

Finasteride and Minoxidil are currently the main treatments for male-pattern baldness, and Minoxidil can also be used to treat female-pattern baldness. However, these treatments can be expensive, they don't work for everyone, they take a long time to work and they only work for as long as they are used, typically working to prevent further hair loss rather than to regrow lost hair. Minoxidil can have significant side effects such as localised dermatitis and systemic side effects such as changes in blood pressure. Finasteride can lower libido and sperm count. Alopecia areata may be treated by steroid injections in the affected area, but these injections need to be frequently repeated to be effective and have significant local side effects such as skin thinning and decreased pigmentation.

Other hair loss treatments include steroid creams, immunotherapy, light treatment, tattooing, hair transplant (natural or artificial) and scalp reduction surgery, although each has their disadvantages, whether that be invasiveness by injection or surgery, the high cost of treatment, side effects due to the drugs used or a delay in the onset of results. A small proportion of patients resort to using hair systems which can turn out to be exceptionally life limiting, expensive and hasten loss of native hair.

A further aspect of the ageing process is a lightening, greying or whitening of the hair, caused by a reduction in the amount of melanin, a pigment, produced by the hair follicles. Premature greying of the hair can also occur, often caused by nutritional deficiencies like vitamin B12 deficiency, severe iron deficiency, chronic protein loss and copper deficiency.

The most common way of restoring hair colour is to use hair colourants. However, this is only a temporary solution to the problem of greying of hair. Other topical treatments that are currently being explored for preventing and/or reversing greying of the hair include photoprotectors and topical melatonin, as well as oral supplementation with L-cysteine and L-methionine. However, these treatments are highly unreliable, temporary and there is little evidence that they actually reverse greying.

Despite the above discussed approaches for treating hair loss and for darkening hair colour, there remains a need for alternative active agents/compounds and compositions comprising them for improving hair growth and promoting hair restoration, and/or for preventing and/or reversing the greying of hair. In particular, there is a need for compounds and compositions that can penetrate the skin in effective amounts, that are cost-effective, that are easy to use and apply, that have minimal or no side effects, that are fast-acting, that are effective with intermittent use, that maintain the gains on discontinuation of the product, and that are well-tolerated and painless.

The inventor of the present invention has previously developed a drug delivery preparation comprising at least one anti-tumour drug (the drug typically used for treating malignant skin cancers, vulval intraepithelial neoplasia, vulval squamous cell carcinoma, actinic keratoses, keratoacanthomas, Kaposi sarcoma, Bowen's disease, and benign tumours of viral aetiology), which enables the drug to penetrate a patient's skin in effective amounts and in a more efficient manner than previously achievable (UK Patent Publication No. GB 2398495 A). It has now surprisingly been found that such a drug delivery preparation can be used for hair rejuvenation and hair restoration, in particular to promote hair generation and/or hair growth, to treat and/or prevent hair loss, and/or to prevent and/or reverse the greying of hair.

Accordingly, the present invention seeks to overcome or at least alleviate one or more of the problems found in the prior art.

SUMMARY OF THE INVENTION

In a first aspect, the present invention provides bleomycin for use in the treatment and/or prevention of hair loss.

The bleomycin may be selected from the group consisting of: bleomycin A2; bleomycin B2; bleomycin A2 and bleomycin B2; bleomycin A5; bleomycin A5 and bleomycin B2. Suitably, the bleomycin may be bleomycin A2 and bleomycin B2.

In a second aspect, the present invention provides a composition comprising bleomycin for use in the treatment and/or prevention of hair loss.

The bleomycin may be selected from the group consisting of: bleomycin A2; bleomycin B2; bleomycin A2 and bleomycin B2; bleomycin A5; bleomycin A5 and bleomycin B2. Suitably, the bleomycin may be bleomycin A2 and bleomycin B2.

The composition may further comprise a topical carrier for the bleomycin. The carrier may comprise a lipid and a surfactant. The carrier may be an elastic liposome, a lipid emulsion or a lipid nanoparticle. The surfactant may be a cholate.

The bleomycin may be present in the composition in an amount ranging from about 0.01 percent by weight to about 10 percent by weight.

The composition may be administered or applied to an area to be treated on a subject from one to three times a day for a duration of one day to one year.

The composition may be in the form of a cream, an ointment, a lotion, a gel, a foam, a liquid, a solution, a suspension, a balm, a spray, a wax or a paste.

The hair loss may be associated with or caused by any one or more of the following diseases, disorders or conditions: male-pattern baldness; female-pattern baldness; all types of alopecia including alopecia areata, scarring alopecias and telogen effluvium; vitamin or mineral deficiencies; trichotillomania; lupus erythematosus; hypothyroidism; hyperthyroidism; diabetes; or sarcoidosis.

In a third aspect, the present invention provides a non-therapeutic method for promoting hair generation and/or hair growth, the method comprising administering or applying bleomycin or a composition comprising bleomycin to an area on the subject where the promotion of hair generation and/or hair growth is desired.

In a fourth aspect, the present invention provides a non-therapeutic method for darkening hair, the method comprising administering or applying bleomycin or a composition comprising bleomycin to an area on the subject where darkening of hair is desired.

The bleomycin may be selected from the group consisting of: bleomycin A2; bleomycin B2; bleomycin A2 and bleomycin B2; bleomycin A5; bleomycin A5 and bleomycin B2. Suitably, the bleomycin may be bleomycin A2 and bleomycin B2.

The composition may further comprise a topical carrier for the bleomycin. The carrier may comprise a lipid and a surfactant. The carrier may be an elastic liposome, a lipid emulsion or a lipid nanoparticle. The surfactant may be a cholate.

The bleomycin may be present in the composition in an amount ranging from about 0.01 percent by weight to about 10 percent by weight.

The composition may be applied to an area to be treated on a subject from one to three times a day for a duration of one day to one year.

The composition may be in the form of a cream, an ointment, a lotion, a gel, a foam, a liquid, a solution, a suspension, a balm, a spray, a wax or a paste.

It will be appreciated that any features of one aspect or embodiment of the invention may be combined with any combination of features in any other aspect or embodiment of the invention, unless otherwise stated, and such combinations fall within the scope of the claimed invention.

BRIEF DESCRIPTION OF THE DRAWINGS

The disclosure is further illustrated by reference to the accompanying drawings in which.

DETAILED DESCRIPTION OF THE INVENTION

All references cited herein are incorporated by reference in their entirety. Unless otherwise defined, all technical and scientific terms used herein have the same meaning as commonly understood by one of ordinary skill in the art to which this invention belongs.

In order to assist with the understanding of the invention several terms are defined herein.

The term "hair loss" refers to a loss of hair from part of the head or body, in particular where the number of hairs is smaller than that of a normal hair level without a particular limitation. The hair may be lost at a frequency higher than that associated with healthy or standard hair renewal. It also refers to a weakening of the hair. The hair loss may be caused by any disease or disorder, a symptom or consequence of which is that the number of hairs in a particular area is decreased or where the hair is weakened. The hair loss may also be due to any other circumstances, such as the side effect of medications (e.g., chemotherapeutic drugs).

The term "hair generation" refers to the generation of hair and "hair growth" refers to hair growth or hair regrowth.

The terms "preventing" or "prevention" refer to all activities which suppress, inhibit or delay hair loss by administering the compounds or compositions of the present disclosure.

The terms "treating" or "treatment" refer to all activities which improve or reverse hair loss by administering the compounds or compositions of the present disclosure.

The present invention relates to bleomycin and compositions comprising bleomycin for use in the treatment and/or prevention of hair loss, or for promoting hair growth and/or hair generation (e.g., medical use or therapeutic use or non-cosmetic use of bleomycin and compositions comprising bleomycin). The present invention also relates to the use of bleomycin or a composition comprising bleomycin for the manufacture of a medicament for the treatment and/or prevention of hair loss, or for promoting hair growth and/or hair generation. The present invention further relates to a method for the treatment or prevention of hair loss, or for promoting hair growth and/or hair generation, or for darkening hair, in a subject in need thereof, the method comprising administering or applying bleomycin or a composition comprising bleomycin to an affected area on the subject. The present invention also relates to a non-therapeutic (e.g., cosmetic) method for promoting hair generation and/or hair growth, the method comprising administering or applying bleomycin or a composition comprising bleomycin to an area on the subject where the promotion of hair generation and/or hair growth is desired. The present invention further relates to a non-therapeutic (e.g., cosmetic) method for darkening hair, the method comprising administering or applying bleomycin or a composition comprising bleomycin to an area on the subject where darkening or hair is desired.

The term "bleomycin" refers to a group of natural glycopeptide antibiotics produced by *Streptomyces verticillus*. It includes bleomycins A and bleomycins B, derivatives of these bleomycins, analogues of these bleomycins, and biologically active metabolites of these bleomycins. Bleomycins A and B are further subdivided into bleomycin A1-6 and B1-5. Bleomycin sulphate is an example of a bleomycin and comprises bleomycin A2 and bleomycin B2. The structure of bleomycin A2 is reproduced below:

The term "bleomycin" additionally refers to pingyangmycin, also known as bleomycin A5, which is produced by a variety of *Streptomyces verticillus, pingyangesis* n. sp., and is extensively used in China as a substitution for bleomycin A2. The structure of pingyangmycin is reproduced below:

Bleomycin is cytotoxic and is primarily used to treat cancer. It can also be used to help prevent the recurrence of a pleural effusion due to cancer. For each form of bleomycin, the mode of action in the treatment of cancer is well-understood and is directed to the ability of bleomycin to bind with DNA and subsequently cause breaks in the DNA sequence, which subsequently leads to cell death. Of the different types of bleomycin, approximately 60-70 percent of the type used clinically for cancer treatment is bleomycin A2 and approximately 20-30 percent of the remainder of clinical product is in the form of bleomycin B2, with other analogy comprising about 5 percent of the total bleomycin usage. Any form of bleomycin may be used in the present invention. Suitably the bleomycin is (active) bleomycin A2. Suitably, the bleomycin is (active) bleomycin B2. Suitably, the bleomycin is a combination of (active) bleomycin A2 and (active) bleomycin B2. Suitably, the bleomycin is (active) bleomycin A5. Suitably, the bleomycin is a combination of (active) bleomycin A5 and (active) bleomycin B2. Mixtures of active and inactive bleomycins may be used. For example, the bleomycin may comprise active bleomycin A2, active bleomycin B2, and inactive bleomycin A2.

Many drugs and compounds can have difficulty in penetrating skin in effective amounts. Indeed, topical transcutaneous delivery of water-soluble bleomycin can be challenging because of its inability to penetrate the stratum corneum due to its highly polar positively charged molecule (a large, metal-binding glycopeptide molecule), which compromises penetration into the epidermis. Therefore, in order to more effectively administer bleomycin it can be beneficial to use a carrier for the bleomycin.

Compositions disclosed herein may thus comprise a carrier for the bleomycin. The carrier can be any carrier that is suitable for topical use and which enables bleomycin to penetrate a patient's/subject's skin in effective amounts.

The carrier may comprise a lipid and a surfactant. The lipid may be such that it is able to entrap the bleomycin and the surfactant may be such that it confers elastic properties to the carrier. Such a carrier provides increased bleomycin encapsulation efficiency, enhanced bleomycin permeation and penetration into or across the skin, improved bleomycin release, as well as stability.

Suitably, the carrier may be an elastic liposome. Elastic liposomes are highly deformable and are also known as deformable liposomes, ultradeformable liposomes, flexible liposomes, and ultraflexible liposomes.

FIG. 1 is a pictorial representation of how an elastic liposome is used to entrap bleomycin. As can be seen from FIG. 1, lipids are the building blocks of biological membranes. Liposomes are generated when lipid molecules are dispersed in water. The liposomes entrap the bleomycin, a water-soluble compound, for subsequent delivery to the area of skin of a subject where treatment for hair loss and/or greying is desired.

Other types of carriers may be, for example, lipid emulsions or lipid nanoparticles.

Suitably, the surfactant may be a cholate, for example sodium cholate. Other types of surfactants that may be used are, for example Tween 80 or Triton-X (Registered Trade Marks). Tween 80 is a polyoxyethylene sorbitan monooleate. Triton-X is produced from octylphenol polymerised with ethylene oxide.

The surfactant may be present in the composition in an amount ranging from about 0.1 percent by weight to about 2 percent by weight.

The lipid component of the carrier may be any suitable phospholipid or mixture of phospholipids, for example lecithin. Suitable lipids may include phosphatidylcholine, phosphatidylethanolamine, phosphatidylinositol, phosphatidylserine and phosphatidic acid, for example. Suitably, the lipid may be a phosphatidylcholine.

The lipid may be present in the composition in an amount ranging from about 1 percent by weight to about 10 percent by weight.

The composition may further comprise an excipient. Any suitable and appropriate type of excipient may be used. For example, the excipient may be a preservative, or more generally, an excipient which has a beneficial effect on the stability and controlled release of the bleomycin from the carrier.

The compositions disclosed herein may be formulated in any suitable and appropriate form for topical application. For example, the compositions may be in the form of a cream, an ointment, a lotion, a gel, a foam, a liquid, a solution, a suspension, a balm, a spray, a wax, or a paste.

Advantageously, the compositions may be administered directly onto the skin by manual application or via a simple device, such as a roller or a spray (e.g., a spray aerosol or pump).

It is also possible to use, for example, a derma roller, an air-jet or other ablative instrument, such as an ablative laser, in conjunction with bleomycin and compositions comprising bleomycin as disclosed herein, to encourage the penetration and permeation of bleomycin and compositions comprising bleomycin into or across the skin.

The bleomycin and compositions comprising bleomycin as disclosed herein may also be deployed through a dermal patch that is placed on the skin to deliver the bleomycin to hair follicles.

Alternatively, bleomycin and compositions comprising bleomycin may be administered to an area to be treated on a subject by injection, typically by superficial injection into an affected area of skin on the subject, suitably the hair follicle area under the surface of the skin. As per the topical bleomycin compositions described herein, the injectable bleomycin can be mixed with other suitable carriers and/or excipients and formulated into a suitable form for injectable administration.

The compositions disclosed herein may comprise further components/ingredients which will aid in the formulation and use of the compositions, such as binders, emollients, humectants, preservatives, lubricants, colourants, solvents, alcohols, perfumes, and the like.

The compositions, as well as the manner by which they are applied, are specifically formulated for localised application on discrete areas of the body where hair restoration and/or hair darkening is sought, and are specifically formulated and intended to be applied in a manner that does not involve any systemic distribution of the active bleomycin agent. The compositions are simple to administer and provide effective treatment on only those portions of the body selected.

The bleomycin may be present in the composition in an amount ranging from about 0.01 percent by weight to about 10 percent by weight, suitably from about 0.02 percent by weight to about 5 percent by weight, suitably from about 0.04 percent by weight to about 2 percent by weight, suitably from about 0.06 percent by weight to about 1 percent by weight, suitably from about 0.08 percent by weight to about 0.5 percent by weight, suitably from about 0.1 percent by weight to about 0.4 percent by weight. Suitably, the bleomycin may be present in the composition in an amount of about 0.2 percent by weight.

The composition may be applied (or administered) once a day or up to several times a day for a period of days, weeks, months or up to a year on the area to be treated until the desired result is achieved. Suitably, the composition may be applied from one to three times a day for a duration of one day to one year. Suitably, the composition may be applied from one to three times a day for up to six months. Suitably, the composition may be applied from one to three times a day for up to three months. Suitably, the composition may be applied twice a day for up to one year. Suitably, the composition may be applied twice a day for a period of up to six months. Suitably, the composition may be applied twice a day for a period of up to three months. Suitably, the composition may be applied twice a day for up to one month. Suitably, the composition may be applied twice a day for three weeks. Suitably, the composition may be applied twice a day for three weeks in every month for a period of from three months up to one year.

Advantageously, when use (either non-therapeutic/cosmetic or therapeutic/non-cosmetic), or application of the compositions disclosed herein, or treatment using the compositions disclosed herein, is stopped or paused, no loss of hair is observed and the hair that has been gained during the course of use, treatment or application remains in place. Therefore, the present invention is beneficial over existing treatments such a Minoxidil and Finasteride where loss of hair occurs when the treatment is stopped. Furthermore, the compositions disclosed herein are faster at generating hair growth than Minoxidil and Finasteride.

The topical formulations and compositions disclosed herein are also easy to apply, non-invasive, safe, well-tolerated, painless and cost-effective. No apparent side effects on normal tissue structures are observed. The compositions, in particular the active bleomycin agent of the compositions, are also able to penetrate the skin in effective amounts and in a highly efficient manner.

It is not known with certainty the actual mechanism by which the bleomycin and compositions comprising bleomycin disclosed herein bring about the recognised improvement in hair growth and restoration. However, since neither bleomycin alone nor compositions comprising bleomycin, in particular liposomal compositions comprising bleomycin, are observed to cause any damage to normal tissue structures to which they are topically applied (i.e. areas where hair growth is desired) and since both are shown to improve hair growth (rather than halt it), it is theorised that bleomycin and the compositions comprising bleomycin disclosed herein are not cytotoxic to hair cells and are unlikely to be causing any DNA damage to the hair cells. This is in contrast with cancerous skin/cells to which bleomycin is known to be cytotoxic.

The bleomycin and compositions comprising bleomycin as disclosed herein can be used on healthy non-cancerous skin to improve/restore hair growth or to darken hair and can also be used on cancerous skin/cells to improve/restore hair growth or to darken hair. Suitably, the bleomycin and compositions comprising bleomycin as disclosed herein can be used on healthy non-cancerous skin to improve/restore hair growth or to darken hair. For example, in a non-therapeutic method for promoting hair generation and/or hair growth as described herein, the bleomycin or composition comprising bleomycin may be applied to non-cancerous skin in an area on the subject where the promotion of hair generation and/or hair growth is desired. For example, in a non-therapeutic method for darkening hair as described herein, the bleomycin or composition comprising bleomycin may be applied to non-cancerous skin in an area on the subject where darkening of hair is desired.

The subject or patient to be treated using the compounds, compositions and methods described herein will usually be a human but may be an animal in some cases.

The subject may be a subject in whom hair loss is or may be in progress and is desirous of hair restoration and rejuvenation. The subject may be suffering from a medical disease, condition or disorder which is causing the hair loss. Alternatively, the subject may not be suffering from a medical disease, condition or disorder associated with hair loss, but is one desirous of promoting hair growth and generation and improving the thickness and/or length of hair.

The subject may be a subject desirous of preventing and/or reversing the greying of hair.

The compounds, compositions and methods described herein are typically used on the scalp, but can also be used on the eyebrows and beard, or other places on the body where hair is usually present and is desired to be restored and/or where it is desired to turn hair darker.

The compounds, compositions and methods described herein can be used for hair restoration and hair rejuvenation, in particular for treating or preventing hair loss, treating or preventing weakened hair, promoting hair growth and hair generation, improving hair thickness and density, and improving hair length.

The hair loss may be caused by any disease or disorder, a symptom or consequence of which is that the number of hairs in a particular area is decreased. For example, the hair loss may be associated with or caused by any one or more of the following diseases, disorders or conditions: male-pattern baldness; female-pattern baldness; all types of alopecia including alopecia areata, scarring alopecias and telogen effluvium; vitamin or mineral deficiencies; trichotillomania; lupus erythematosus; hypothyroidism; hyperthyroidism; diabetes; or sarcoidosis.

The hair loss may also be due to any other circumstances, such as the side effect of medications (e.g., chemotherapeutic drugs) or radiation therapy, stress, weight loss, tightly pulled hair, stressing hair treatments (such as dyeing or bleaching, or straightening or curling with mechanical apparatus), hair fragility, menopause, or combinations thereof.

The compounds, compositions and methods described herein are suitable for both therapeutic (e.g., medical or non-cosmetic) uses and non-therapeutic (e.g., cosmetic) uses in treating and/or preventing hair loss and promoting hair generation and/or hair growth, e.g., the compositions described herein may be pharmaceutical compositions or non-pharmaceutical compositions. For example, the present invention suitably relates to bleomycin and compositions comprising bleomycin for medical (therapeutic) use in the treatment and/or prevention of hair loss.

In addition, the compounds, compositions, and methods disclosed herein can be used for darkening hair colour, in particular for turning grey or white hair darker or black.

The present disclosure is further exemplified in the following clauses:
1. Bleomycin for use in the treatment and/or prevention of hair loss.
2. Bleomycin for the use according to clause 1, wherein the bleomycin is selected from the group consisting of: bleomycin A2; bleomycin B2; bleomycin A2 and bleomycin B2; bleomycin A5; bleomycin A5 and bleomycin B2.

3. Bleomycin for the use according to clause 1 or clause 2, wherein the bleomycin is bleomycin A2 and bleomycin B2.
4. A composition comprising bleomycin for use in the treatment and/or prevention of hair loss.
5. The composition for the use according to clause 4, wherein the bleomycin is selected from the group consisting of: bleomycin A2; bleomycin B2; bleomycin A2 and bleomycin B2; bleomycin A5; bleomycin A5 and bleomycin B2.
6. The composition for the use according to clause 4 or clause 5, wherein the bleomycin is bleomycin A2 and bleomycin B2.
7. The composition for the use according to any of clauses 4 to 6, wherein the composition further comprises a topical carrier for the bleomycin.
8. The composition for the use according to clause 7, wherein the carrier comprises a lipid and a surfactant.
9. The composition for the use according to clause 7 or clause 8, wherein the carrier is an elastic liposome, a lipid emulsion or a lipid nanoparticle.
10. The composition for the use according to any of clauses 7 to 9, wherein the carrier is an elastic liposome.
11. The composition for the use according to any of clauses 8 to 10, wherein the surfactant is a cholate.
12. The composition for the use according to any of clauses 4 to 11, wherein the bleomycin is present in the composition in an amount ranging from about 0.01 percent by weight to about 10 percent by weight.
13. The composition for the use according to any of clauses 4 to 12, wherein the composition is administered or applied to an area to be treated on a subject from one to three times a day for a duration of one day to one year.
14. The composition for the use according to any of clauses 4 to 13, wherein the composition is in the form of a cream, an ointment, a lotion, a gel, a foam, a liquid, a solution, a suspension, a balm, a spray, a wax or a paste.
15. The composition for the use according to any of clauses 1 to 14, wherein the hair loss is associated with or caused by any one or more of the following diseases, disorders or conditions: male-pattern baldness; female-pattern baldness; all types of alopecia including alopecia areata, scarring alopecias and telogen effluvium; vitamin or mineral deficiencies; trichotillomania; lupus erythematosus; hypothyroidism; hyperthyroidism; diabetes; or sarcoidosis.
16. Use of bleomycin for the manufacture of a medicament for the treatment and/or prevention of hair loss.
17. Use of bleomycin according to clause 16, wherein the bleomycin is selected from the group consisting of: bleomycin A2; bleomycin B2; bleomycin A2 and bleomycin B2; bleomycin A5; bleomycin A5 and bleomycin B2.
18. Use of bleomycin according to clause 16 or clause 17, wherein the bleomycin is bleomycin A2 and bleomycin B2.
19. Use of a composition comprising bleomycin for the manufacture of a medicament for the treatment and/or prevention of hair loss.
20. The use according to clause 19, wherein the bleomycin is selected from the group consisting of: bleomycin A2; bleomycin B2; bleomycin A2 and bleomycin B2; bleomycin A5; bleomycin A5 and bleomycin B2.
21. The use according to clause 19 or clause 20, wherein the bleomycin is bleomycin A2 and bleomycin B2.
22. The use according to any of clauses 19 to 21, wherein the composition further comprises a topical carrier for the bleomycin.
23. The use according to clause 22, wherein the carrier comprises a lipid and a surfactant.
24. The use according to clause 22 or clause 23, wherein the carrier is an elastic liposome, a lipid emulsion or a lipid nanoparticle.
25. The use according to any of clauses 22 to 24, wherein the carrier is an elastic liposome.
26. The use according to any of clauses 23 to 25, wherein the surfactant is a cholate.
27. The use according to any of clauses 19 to 26, wherein the bleomycin is present in the composition in an amount ranging from about 0.01 percent by weight to about 10 percent by weight.
28. The use according to any of clauses 19 to 27, wherein the composition is applied to an area to be treated on a subject from one to three times a day for a duration of one day to one year.
29. The use according to any of clauses 19 to 28, wherein the composition is in the form of a cream, an ointment, a lotion, a gel, a foam, a liquid, a solution, a suspension, a balm, a spray, a wax or a paste.
30. The use according to any of clauses 16 to 29, wherein the hair loss is associated with or caused by any one or more of the following diseases, disorders or conditions: male-pattern baldness; female-pattern baldness; all types of alopecia including alopecia areata, scarring alopecias and telogen effluvium; vitamin or mineral deficiencies; trichotillomania; lupus erythematosus; hypothyroidism; hyperthyroidism; diabetes; or sarcoidosis.
31. A method for the treatment and/or prevention of hair loss in a subject in need thereof, the method comprising administering or applying bleomycin or a composition comprising bleomycin to an affected area on the subject.
32. A non-therapeutic method for promoting hair generation and/or hair growth, the method comprising administering or applying bleomycin or a composition comprising bleomycin to an area on the subject where the promotion of hair generation and/or hair growth is desired.
33. A non-therapeutic method for darkening hair, the method comprising administering or applying bleomycin or a composition comprising bleomycin to an area on the subject where darkening of hair is desired.
34. The method according to any of clauses 31 to 33, wherein the bleomycin is selected from the group consisting of: bleomycin A2; bleomycin B2; bleomycin A2 and bleomycin B2; bleomycin A5; bleomycin A5 and bleomycin B2.
35. The method according to any of clauses 31 to 34, wherein the bleomycin is bleomycin A2 and bleomycin B2.
36. The method according to any of clauses 31 to 35, wherein the composition further comprises a topical carrier for the bleomycin.
37. The method according to clause 36, wherein the carrier comprises a lipid and a surfactant.
38. The method according to clause 36 or clause 37, wherein the carrier is an elastic liposome, a lipid emulsion or a lipid nanoparticle.

39. The method according to any of clauses 36 to 38, wherein the carrier is an elastic liposome.
40. The method according to any of clauses 37 to 39, wherein the surfactant is a cholate.
41. The method according to any of clauses 31 to 40, wherein the bleomycin is present in the composition in an amount ranging from about 0.01 percent by weight to about 10 percent by weight.
42. The method according to any of clauses 31 to 41, wherein the composition is applied to an area to be treated on a subject from one to three times a day for a duration of one day to one year.
43. The method according to any of clauses 31 to 42, wherein the composition is in the form of a cream, an ointment, a lotion, a gel, a foam, a liquid, a solution, a suspension, a balm, a spray, a wax or a paste.
44. The method according to any of clauses 31 and 34 to 43 when dependent on 31, wherein the hair loss is associated with or caused by any one or more of the following diseases, disorders or conditions: male-pattern baldness; female-pattern baldness; all types of alopecia including alopecia areata, scarring alopecias and telogen effluvium; vitamin or mineral deficiencies; trichotillomania; lupus erythematosus; hypothyroidism; hyperthyroidism; diabetes; or sarcoidosis.

EXAMPLES

The invention will now be further illustrated by way of the following non-limiting examples.

Example 1—Preparation of Liposomal Composition

Phosphate buffer was prepared using phosphate buffered saline tablets (Calbiochem).

Sodium cholate and lecithin granules were added to sufficient Absolute Alcohol BP.

The resulting mixture was immersed in a sonicator containing water and sonicated for 10 minutes until the lecithin and sodium cholate were fully dissolved.

Bleomycin sulphate (0.2 g per 100 g of final composition) was added and the resulting solution was shaken and then sonicated for 30 minutes to form liposomes.

The liposomal solution was then poured into a rotary mixing bowl and appropriate agents were added to form a smooth gel or a spray as desired.

Example 2—Subject A

Subject A (a 61-year-old male) was treated with a liposomal bleomycin composition comprising 0.2 percent by weight bleomycin prepared by the method of Example 1 in the form of a liquid spray. The composition was applied to the scalp twice a day for three weeks.

Figure 1:
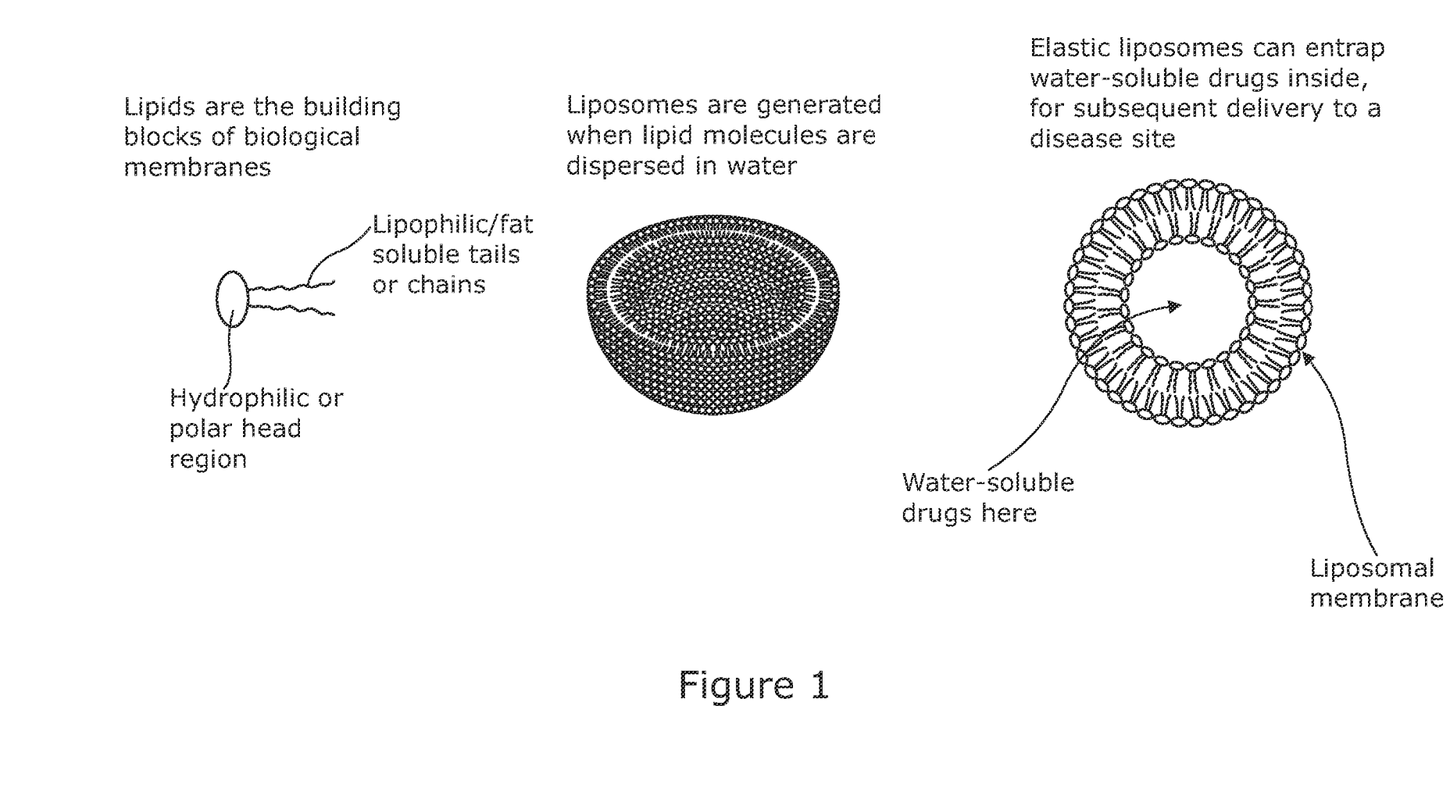
FIG. 1 is a pictorial explanation of how bleomycin can be entrapped in an elastic liposome.
Figure 2:
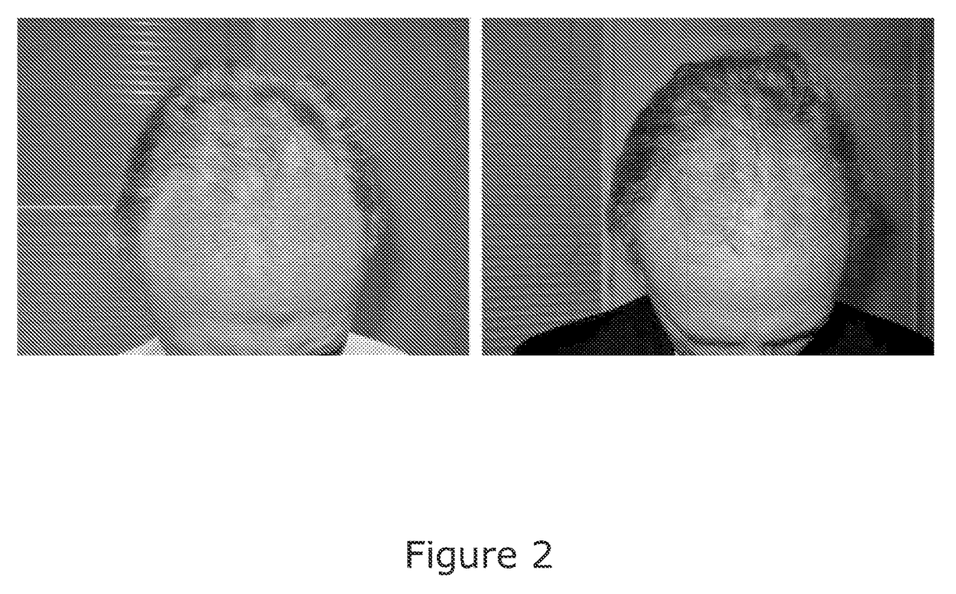
FIG. 2 shows photographs of the scalp of a subject (Subject A) before (left photo) and after (right photo) treatment with a liposomal bleomycin composition disclosed herein.

The results are shown in FIG. 2. The left photo shows the scalp immediately prior to the start of treatment. The right photo shows the scalp four months after the start of treatment. Vellus hair (light, short, fine hair) can be seen turning into terminal hair (longer, thicker, darker hair) and the hair was darker. No loss of gained hair was observed when treatment was stopped as the right photo was taken over three months after treatment had stopped.

Example 3—Subject B

Subject B (a male) was treated with a liposomal bleomycin composition comprising 0.2 percent by weight bleomycin prepared by the method of Example 1 in the form of a liquid spray. The composition was applied to the scalp twice a day for three weeks.

Figure 3:
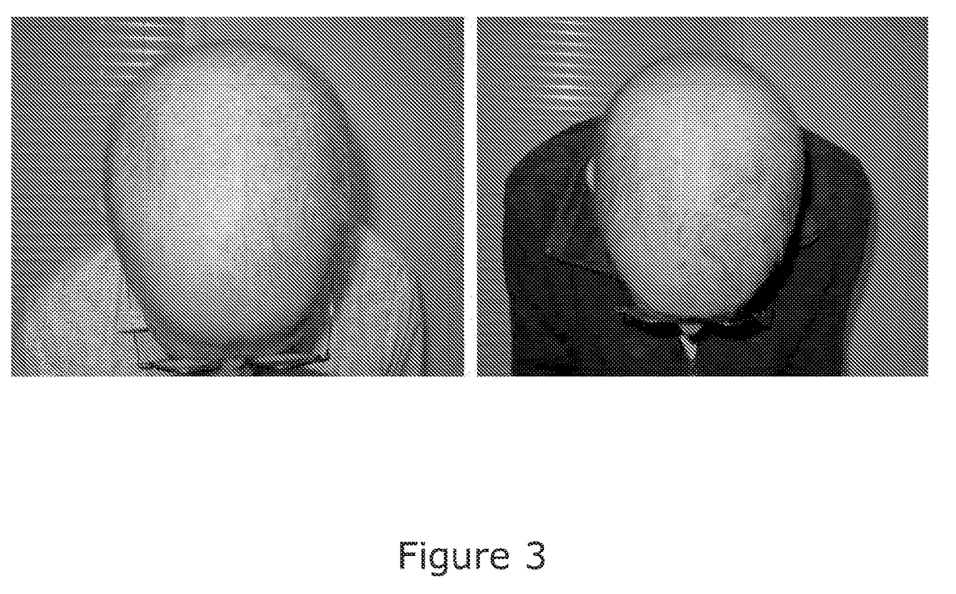
FIG. 3 shows photographs of the scalp of a subject (Subject B) before (left photo) and after (right photo) treatment with a liposomal bleomycin composition disclosed herein.

The results are shown in FIG. 3. The left photo shows the scalp immediately prior to the start of treatment. The right photo shows the scalp three months after the start of treatment. An increase in the number of terminal hairs (longer, thicker, darker hair) was observed and the hair was darker. No loss of gained hair was observed when treatment was stopped as the right photo was taken over two months after treatment had stopped.

Example 4—Subject C

Subject C (a male) presented with dissecting cellulitis and acne keloidalis nuchae. These conditions result in scarring of the scalp and hair loss as well as inflammation, pus and weeping. The subject was initially treated in the standard way with antibiotics, disinfectant washes, topical antibiotics and topical steroids. Once the subject's acne keloidalis nuchae and dissecting cellulitis had settled, the subject was started on a liposomal bleomycin composition comprising 0.2 percent by weight bleomycin prepared by the method of Example 1 in the form of a liquid spray applied twice a day for two weeks to the scarred areas.

Figure 4:
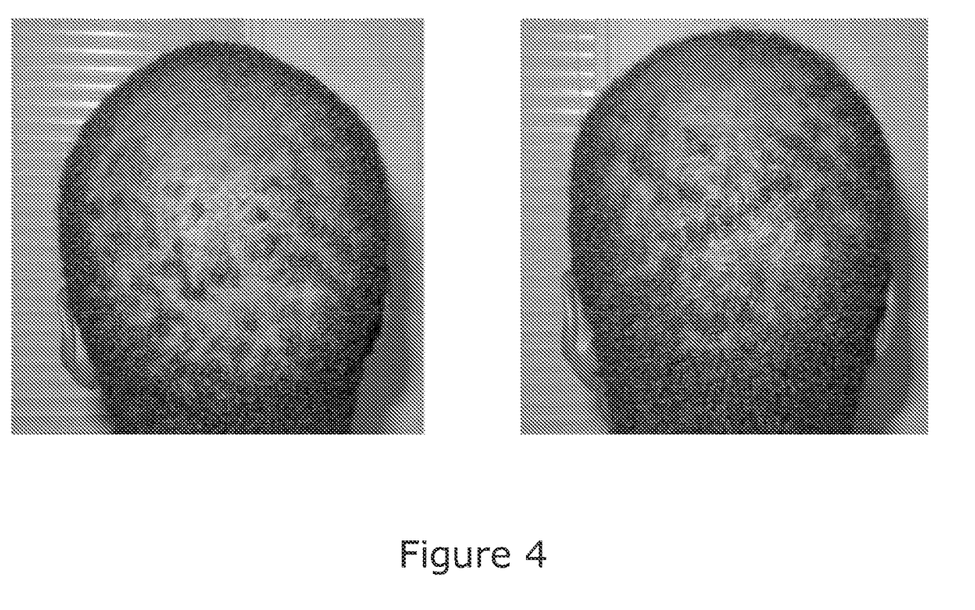
FIG. 4 shows photographs of the scalp of a subject (Subject C) before (left photo) and after (right photo) treatment with a liposomal bleomycin composition disclosed herein.

The results are shown in FIG. 4. The left photo shows the scalp immediately prior to the start of treatment. The right photo shows the scalp two weeks after the start of treatment and hair growth was observed in the scarred areas. This shows that the composition is helpful in treating scarring alopecias.

Example 5—Subject D

Subject D was treated with a liposomal bleomycin composition comprising 0.2 percent by weight bleomycin prepared by the method of Example 1 in the form of a liquid spray applied twice a day for four weeks.

Figure 5:
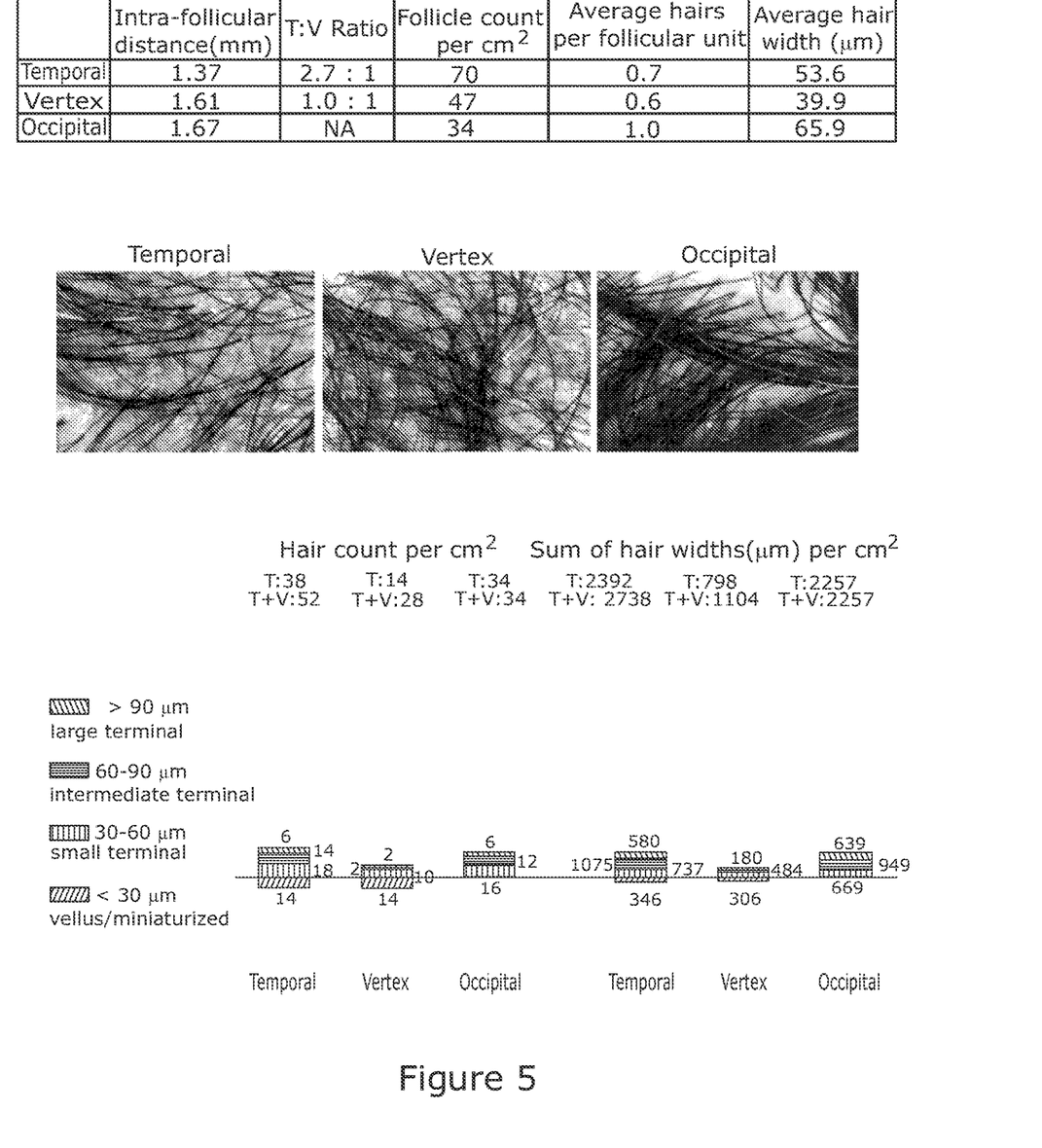
FIG. 5 shows a hair analysis report of the scalp of a subject (Subject D) before treatment with a liposomal bleomycin composition disclosed herein.
Figure 6:
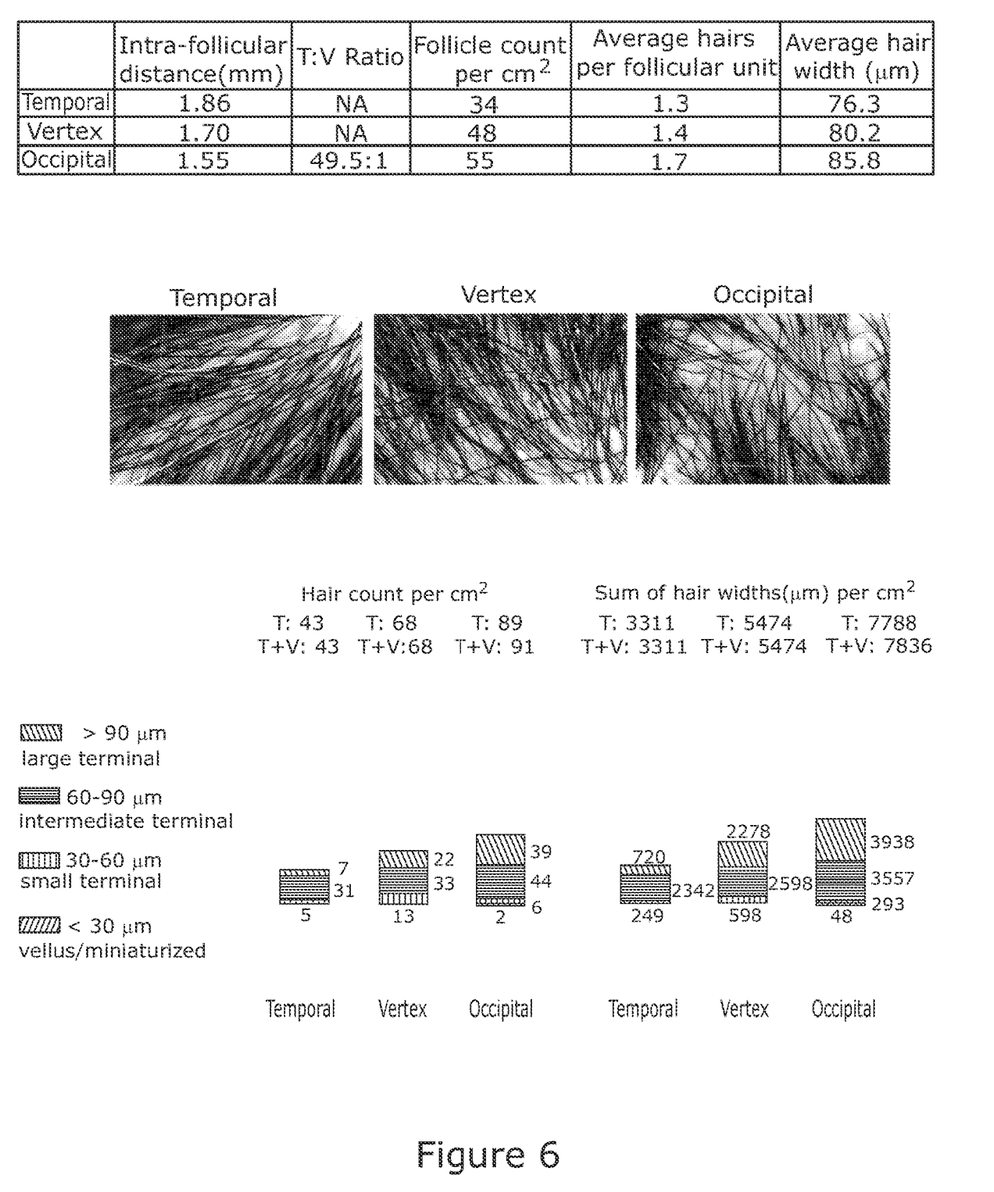
FIG. 6 shows a hair analysis report of the scalp of a subject (Subject D) after treatment with a liposomal bleomycin composition disclosed herein.

As shown in FIG. 5, at baseline immediately prior to the start of treatment, the patient had 14 vellus hairs per $cm^2$, 18 small terminal hairs per $cm^2$, 14 intermediate hairs per $cm^2$ and 6 large terminal hairs per $cm^2$ in the temporal area. As shown in FIG. 6, after four weeks of treatment the number of vellus hairs per $cm^2$ had reduced to zero, the number of small terminal hairs per $cm^2$ had decreased (5), the number of intermediate terminal hairs per $cm^2$ had markedly increased (31) and the number of large terminal hairs per $cm^2$ had slightly increased (7) in the temporal area. There were similar findings for the vertex and occipital areas. The thickness of the hair or the sum of hair width per $cm^2$ increased over the treatment period.

It can be seen that the average hair width in the temporal area was 53.6 µM at baseline and 76.3 µM after 4 weeks of treatment, in the vertex area was 39.9 µM at baseline and 80.2 µM after 4 weeks of treatment, and in the occipital area was 65.9 µM at baseline and 85.8 µM after treatment. This shows that the liposomal bleomycin composition causes hair to thicken. FIGS. 5 and 6 also show that the liposomal bleomycin composition causes the average number of hairs per follicular unit to increase.

Example 6—Subject E

Subject E was treated with a liposomal bleomycin composition comprising 0.2 percent by weight bleomycin prepared by the method of Example 1 in the form of a liquid spray applied once a day at night for four weeks.

Figure 7:
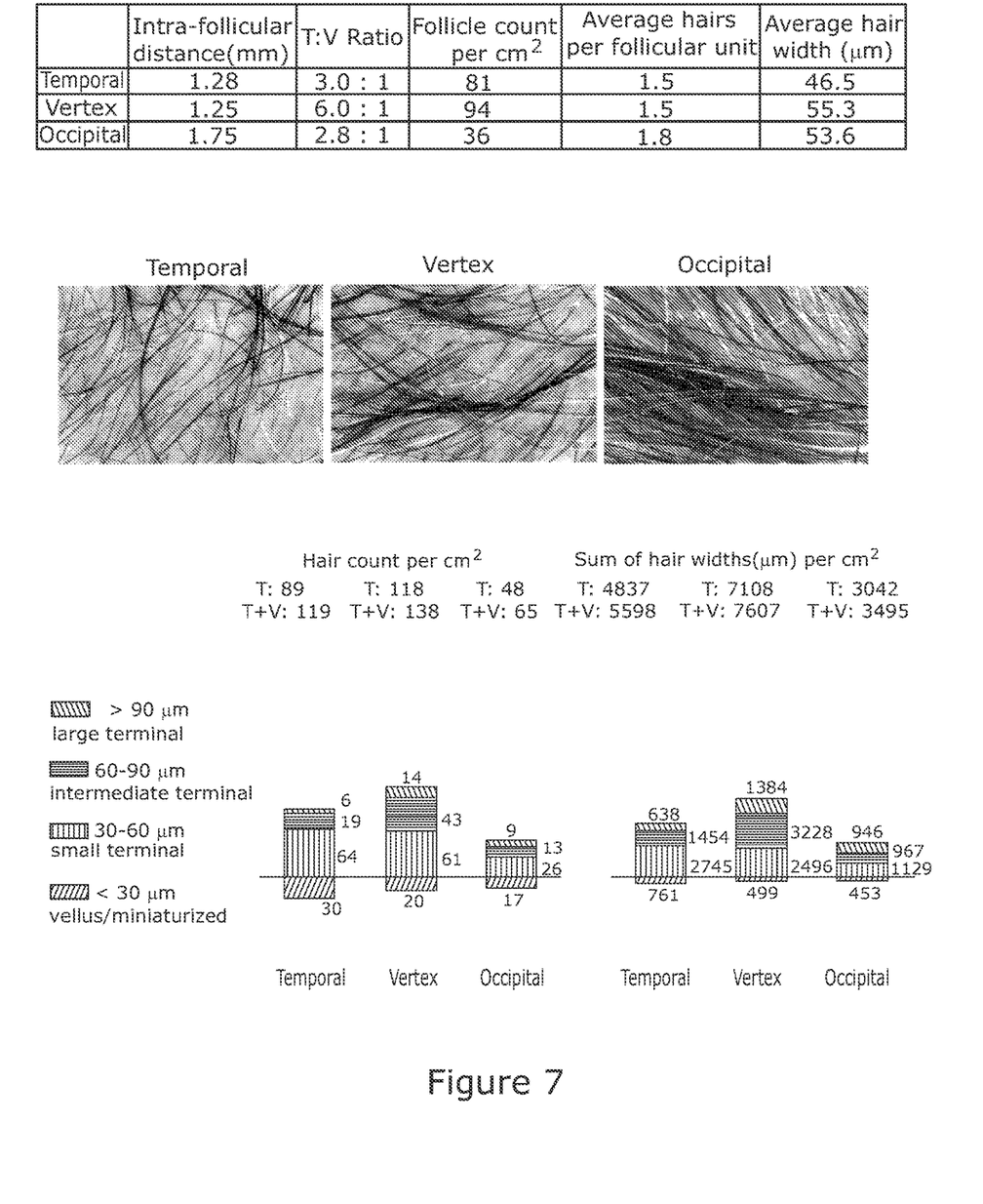
FIG. 7 shows a hair analysis report of the scalp of a subject (Subject E) before treatment with a liposomal bleomycin composition disclosed herein.
Figure 8:
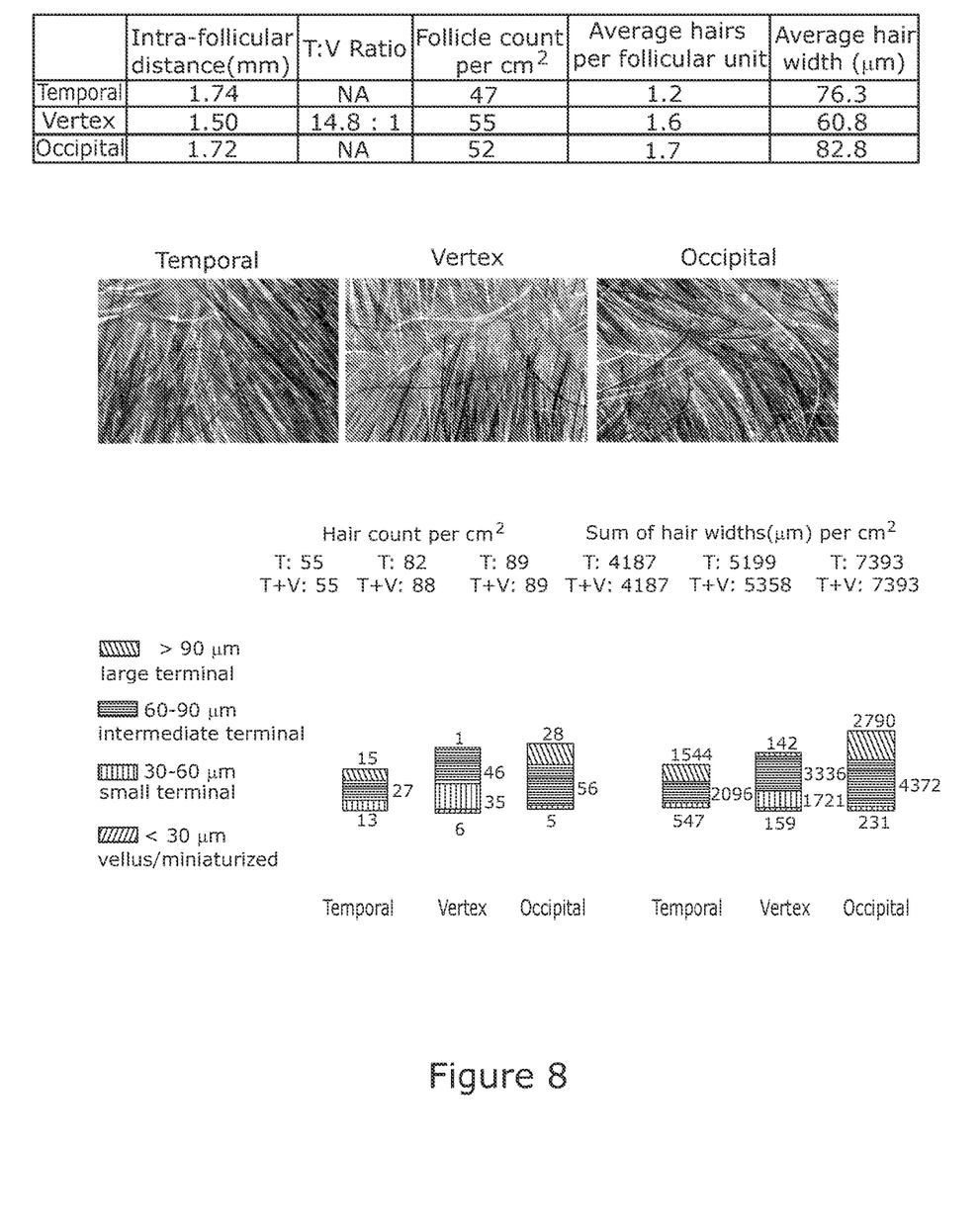
FIG. 8 shows a hair analysis report of the scalp of a subject (Subject E) after treatment with a liposomal bleomycin composition disclosed herein.

As shown in FIG. 7, at baseline immediately prior to the start of treatment, the patient had 30 vellus hairs per cm$^2$, 64 small terminal hairs per cm$^2$, 19 intermediate hairs per cm$^2$ and 6 large terminal hairs per cm$^2$ in the temporal area. As shown in FIG. 8, after four weeks of treatment the number of vellus hairs per cm$^2$ had reduced to zero, the number of small terminal hairs per cm$^2$ had decreased (13), the number of intermediate terminal hairs per cm$^2$ had increased (27) and the number of large terminal hairs per cm$^2$ had increased (15) in the temporal area. There were similar findings for the vertex and occipital areas.

It can be seen that the average hair width in the temporal area was 46.5 µM at baseline and 76.3 µM after 4 weeks of treatment, in the vertex area was 55.3 µM at baseline and 60.8 µM after 4 weeks of treatment, and in the occipital area was 53.6 µM at baseline and 82.8 µM after treatment. This shows that the liposomal bleomycin composition causes hair to thicken.

Although particular embodiments of the invention have been disclosed herein in detail, this has been done by way of example and for the purposes of illustration only. The aforementioned embodiments are not intended to be limiting with respect to the scope of the appended claims, which follow. It is contemplated by the inventor that various substitutions, alterations, and modifications may be made to the invention without departing from the scope of the invention as defined by the claims.

The invention claimed is:

1. A method for the treatment or prevention of hair loss, for promoting hair generation and/or hair growth, and/or darkening hair in a subject in need thereof, the method comprising topically administering or topically applying a composition comprising:
   a) bleomycin, and
   b) a carrier selected from the group consisting of: an elastic liposome, a lipid emulsion, and a lipid nanoparticle;
   to an area on the subject where the treatment or prevention of hair loss, the promotion of hair generation and/or hair growth and/or darkening of hair is desired.

2. The method according to claim 1, wherein the bleomycin is selected from the group consisting of: bleomycin A2; bleomycin B2; bleomycin A2 and bleomycin B2; bleomycin A5; and bleomycin A5 and bleomycin B2.

3. The method according to claim 1, wherein the bleomycin is bleomycin A2 and bleomycin B2.

4. The method according to claim 1, wherein the carrier comprises a lipid and a surfactant.

5. The method according to claim 4, wherein the surfactant is a cholate.

6. The method according to claim 1, wherein the bleomycin is present in the composition in an amount ranging from about 0.01 percent by weight to about 10 percent by weight.

7. The method according to claim 1, wherein the composition is applied to an area to be treated on a subject from one to three times a day for a duration of one day to one year.

8. The method according to claim 1, wherein the composition is in the form of a cream, an ointment, a lotion, a gel, a foam, a liquid, a solution, a suspension, a balm, a spray, a wax or a paste.

9. The method according to claim 1, wherein the hair loss is associated with or caused by any one or more of the following diseases, disorders or conditions: male-pattern baldness; female-pattern baldness; alopecia including alopecia areata; scarring alpoceia; telogen effluvium; vitamin or mineral deficiencies; trichotillomania; lupus erythematosus; hypothyroidism; hyperthyroidism; diabetes; or sarcoidosis.

10. The method according to claim 1, wherein the method is a non-therapeutic method for promoting hair generation and/or hair growth, or for darkening hair.

* * * * *